United States Patent
Washburn et al.

(10) Patent No.: US 6,182,461 B1
(45) Date of Patent: Feb. 6, 2001

(54) PHOTOCATALYTIC OXIDATION ENHANCED EVAPORATOR COIL SURFACE FOR FLY-BY CONTROL

(75) Inventors: Norman A. Washburn, Syracuse, NY (US); Timothy J. Roberts, Tullahoma; Christian C. Herbeck, Manchester, both of TN (US)

(73) Assignee: Carrier Corporation, Syracuse, NY (US)

(*) Notice: Under 35 U.S.C. 154(b), the term of this patent shall be extended for 0 days.

(21) Appl. No.: 09/354,989

(22) Filed: Jul. 16, 1999

(51) Int. Cl.[7] .................................................. F25D 23/00
(52) U.S. Cl. ................................... 62/264; 62/78; 62/317
(58) Field of Search ................................. 62/317, 78, 264

(56) References Cited

U.S. PATENT DOCUMENTS

| | | | |
|---|---|---|---|
| 4,990,313 | * | 2/1991 | Pacosz ................................. 422/121 |
| 5,501,084 | * | 3/1996 | Chang et al. ........................... 62/264 |
| 5,626,020 | * | 5/1997 | Sangster et al. ......................... 62/3.1 |
| 5,755,103 | | 5/1998 | Na et al. . |
| 5,790,934 | | 8/1998 | Say et al. . |
| 5,817,276 | * | 10/1998 | Fencl et al. ............................ 422/24 |
| 5,833,740 | | 11/1998 | Brais . |
| 5,835,840 | | 11/1998 | Goswami . |
| 5,865,959 | | 2/1999 | Meinzer et al. . |
| 5,879,435 | | 3/1999 | Satyapal et al. . |
| 5,891,399 | | 4/1999 | Owesen . |
| 5,902,552 | | 5/1999 | Brickley . |
| 5,911,742 | * | 6/1999 | Akazawa .................................. 62/78 |
| 6,108,476 | * | 8/2000 | Iimura ................................. 385/128 |

* cited by examiner

*Primary Examiner*—William Doerrler
*Assistant Examiner*—Mark Shulman

(57) ABSTRACT

A heat exchanger coil has its fins coated with a photocatalytic semi-conductor material in such a manner that its fins may then be illuminated by UV light to activate the material so as to cause the oxidation of organic pollutants which are on the fin coils themselves or in the air passing therethrough. A preferred photocatalytic semi-conductor material is titanium dioxide, which may be applied to the fin stock prior to the fabrication of the coil.

18 Claims, 2 Drawing Sheets

PHOTOCATALYTIC OXIDATION ENHANCED EVAPORATOR COIL SURFACE FOR FLY-BY CONTROL

This invention relates generally to air conditioning systems and, more particularly, to an air conditioning system having means to treat the air for microbial contaminants.

BACKGROUND OF THE INVENTION

The term "dirty socks syndrome" refers to the offensive smell that can emanate from a poorly maintained air conditioning system in which mold and/or bacteria grow on the indoor coil or in the drain pan. In addition to the undesirable smell, this microbial growth may cause the release of spores and toxins into the air so as to cause allergy related problems. Further, the buildup of mold tends to create maintenance problems because of the dirty coils, an increase in pressure drop, loss of heat exchange efficiency and possibly dirty and plugged drain pans.

Microbial growth can be temporarily treated by using chemicals such as bleach and the like. However, many of the most aggressive cleaning solutions, such as those which are chlorine based, have been banned from use in air conditioning systems. But even where approved biocidal agents are used on coils and drain pans, they do not provide a permanent solution.

The use of UV germicidal lamps have been found to be effective in controlling the growth of microbes in air conditioning systems. One of the most effective ways is to direct the light onto the coil and the drain pan so as to attack the growth directly. One example of such a system is shown in U.S. Pat. No. 5,755,103. There are also systems which filter the impurities from the air and the direct ultraviolet light onto the filter to neutralize the impurities such as are shown in U.S. Pat. Nos. 5,879,435 and 5,891,399. In addition, there is some systems which use the UV light to attack the growth indirectly by the use of a reactor structure which directs the light source on the air flow so as to provide a fly-by control of airborne contaminants. Examples of such systems are shown in U.S. Pat. No. 5,833,740 and U.S. Pat. No. 5,902,552.

More recently, it has been found that the effectiveness of UV irradiation in the conversion of contaminants can be substantially enhanced by the use of a catalyst, such as $TiO_2$, in the reactor environment. U.S. Pat. Nos. 5,835,840; 5,790,934 and 5,865,959 show examples of such systems. It should be mentioned that, while these systems have been shown to be effective in the control of microbial growth, they are relatively expensive to implement since they require a dedicated reactor structure in order to accommodate that single function.

It is therefore an object of the present invention to provide an improved method and apparatus for the treatment of air.

Another object of the present invention is the provision for reducing microbial growth in an air conditioning system.

Yet another object of the present invention is the provision in an air conditioning system for the effective treatment of microbial growth without substantial investment.

Still another object of the present invention is the provision for an air conditioning system, which is capable of treating microbial growth, and which is economical to manufacture and effective in use.

These objects and other advantages become more readily apparent upon reference to the following description when taken in conjunction with the appended drawings.

SUMMARY OF THE INVENTION

Briefly, in accordance with one aspect of the invention, a photocatalytic agent is applied directly to the surface of the fins of the indoor heat exchanger of an air conditioning system, and the fins are irradiated with a UV light source having a wave length which is capable of activating the photocatalyst. The air passing through the evaporator then comes in contact with the photocatalyst and is purified by the activated photocatalyst. In this way, the photocatalyst process is used to simultaneously treat the surface of the heat exchanger and the air passing therethrough.

By another aspect of the invention, the UV light sources are so located that they irradiate both the evaporator coil and drain pan for purposes of directly attacking microbial growth, but also they simultaneously irradiate the coated surfaces of the evaporator coil fin surface such that the contaminated air passing therethrough is also treated.

By yet another aspect of the invention, the evaporator coil fin material is coated with a photocatalyst such as titanium dioxide, either in a pre-coating process wherein the fin is coated prior to being inserted into the heat exchanger structure or in a post-coat process wherein it is coated after it has been assembled into a heat exchanger device.

In the drawings as hereinafter described, a preferred embodiment is depicted. However, various other modifications and alternate constructions can be made thereto without departing from the true spirit and scope of the invention.

DESCRIPTION OF THE PREFERRED EMBODIMENT

Figure 1:
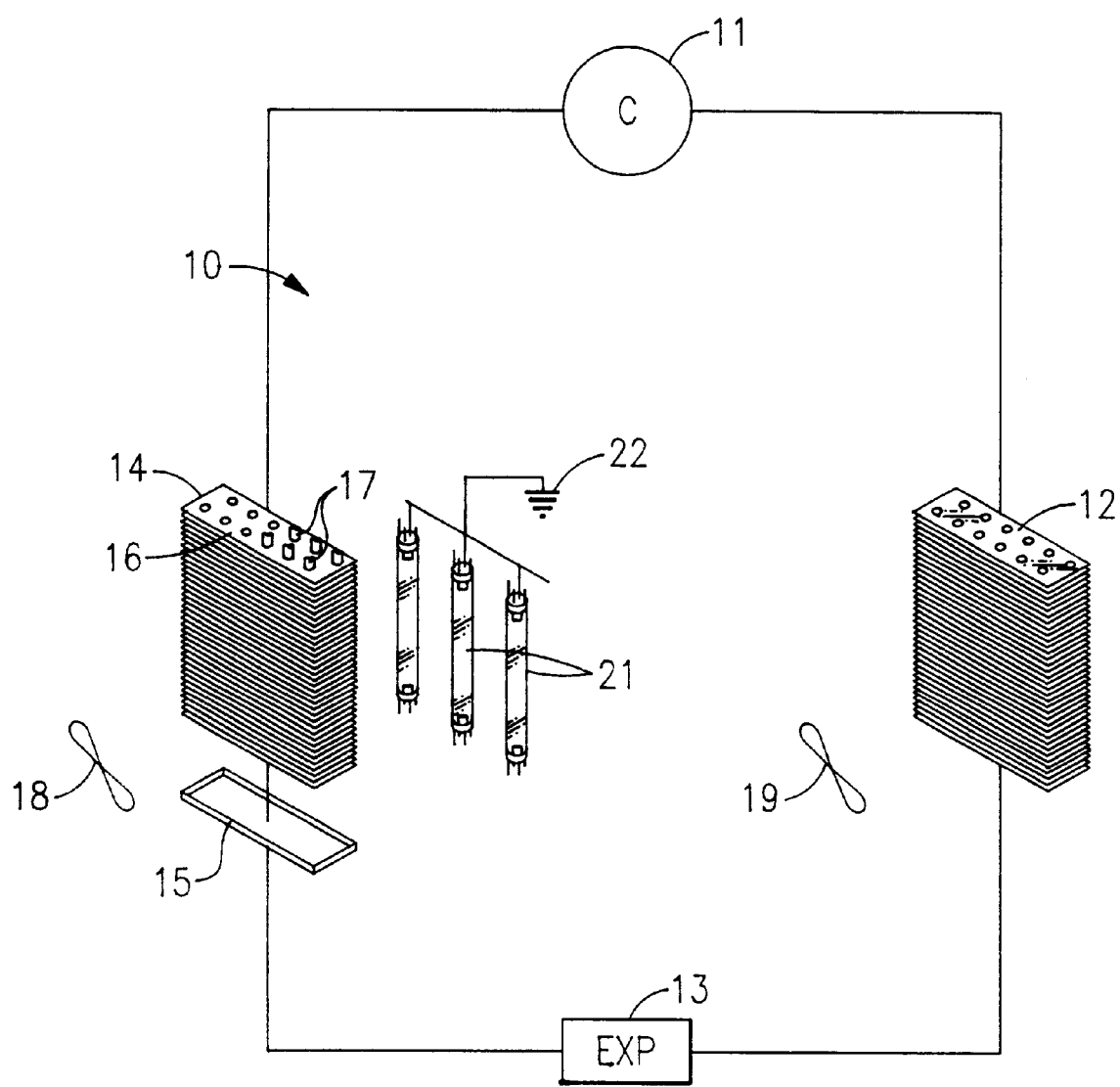
FIG. 1 is a schematic illustration of a air conditioning system having the present invention incorporated therein.

Referring now to FIG. 1, the invention is shown generally at 10 as installed in an otherwise conventional air conditioning system having a compressor 11, a condenser coil 12, an expansion device 13, and an evaporator coil 14.

The evaporator coil 14 includes a plurality of parallel spaced fins 16 through which a plurality of tubes 17, carrying refrigerant in liquid or vapor form, is circulated for purposes of exchanging heat with the air passing through the evaporator coil 14. A fan 18 is provided to circulate the air through the evaporator coil. Similarly, a fan 19 is provided to circulate the outdoor air through the condenser coil 12 for heat exchange purposes. Although shown as blow-through fan they can also be of the drawn-through type. Also, it may be of any type such as a centrifugal blower.

Unlike a conventional evaporator coil, that of the present invention has fins 16 which are coated with a photocatalytic agent such as $TiO_2$ or the like which, when exposed to UV light will be activated to convert microbial contaminants that may reside on the surface of the fins 16, as well as microbial contaminants that are in the air which passes through the evaporator coil 14.

Disposed downstream of the evaporator coil 14 is a plurality of ultraviolet lamps 21, powered by a power source 22, and situated so as to illuminate not only the elements of the evaporator coil 14 and its condensate pan 15, but also the surfaces of the individual fins 16 on which the photocatalyst has been coated. The wave length of the UV lamps is chosen so as to properly activate the photocatalyst such that it tends to purify the microbial growth both on the surfaces of the fins and within the condensate pan 15, but also the microbial contaminants that are caused to flow through the evaporator coil 14 by way of the fan 18.

Figure 2:
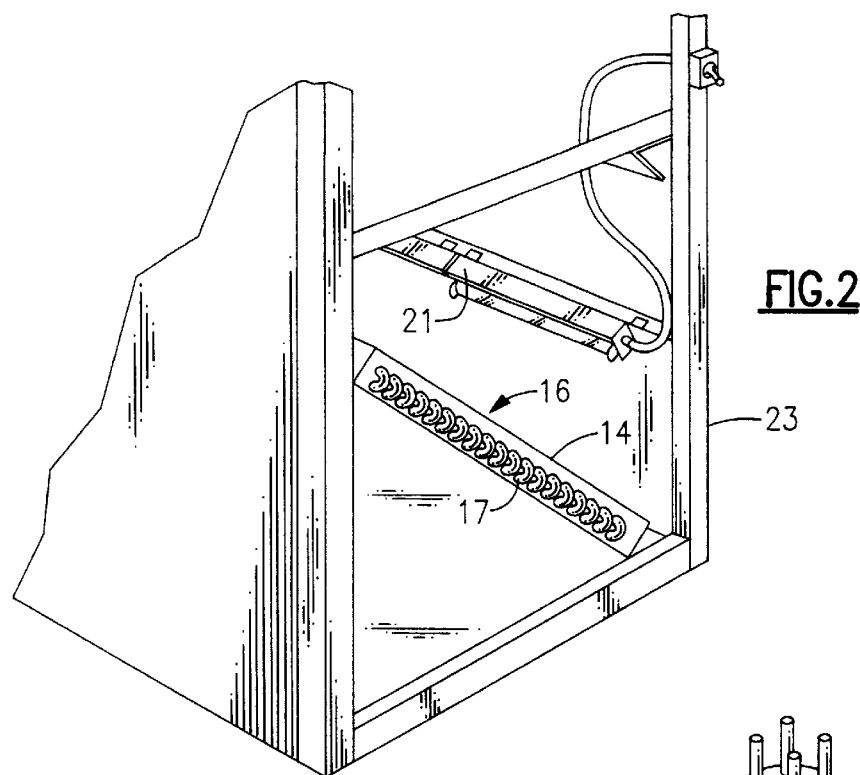
FIG. 2 is a simplified perspective view of a fan coil with the present invention incorporated therein.

In FIG. 2, there is shown a fan coil unit 23 with the present invention incorporated therein. Here, an evaporator coil 14, with its tubes 17 and fins 16, is disposed at an oblique angle in the lower portion of the fan coil unit 23. The fins 16 are coated with a photocatalytic semi-conductor as previously described. A blower (not shown) is located in the upper portion of the fan coil 23 and acts to draw air up through the evaporator coil 14 to be cooled and purified. An ultraviolet lamp 21 is located downstream of the evaporator coil 14 and is aligned with its axis being substantially in parallel relationship with the tubes 17 as shown. In this way, the lamp 21 acts to irradiate the surfaces of the fins 16 which, in the presence of water vapor, tend to thereby form hydroxial radicals which, in turn, oxidizes the organic pollutants on the fins 16 and also those which are entrained in the air flowing through the coil 14.

Figure 3:
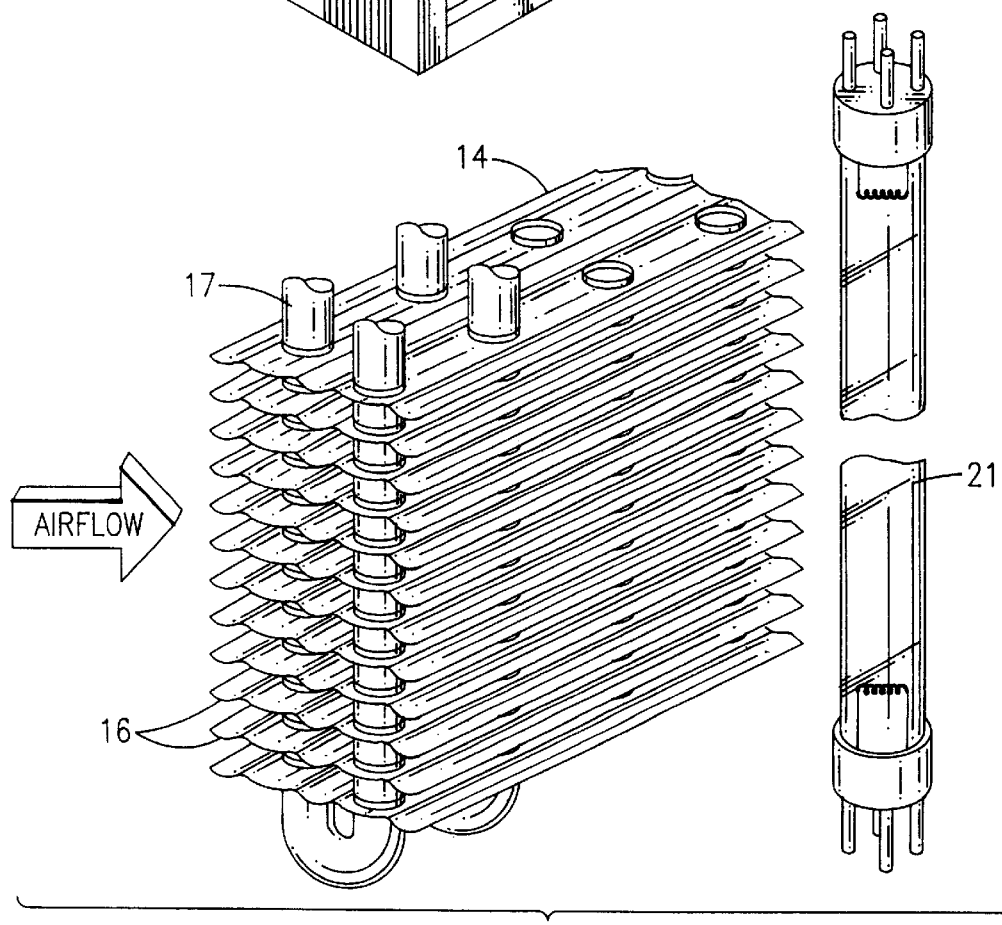
FIG. 3 is schematic view of the coil portion of the present invention incorporated herein.

FIG. 3 shows an enlarged view of the coil 14 with its parallel fins 16 and refrigerant carrying tubes 17. The particular coil 14 shown is a two row coil (i.e. with two rows of tubes across the thickness of the coil in the direction of the air flow. However, it should be recognized that any number of single row or multiple row coils can be used. As will be seen, the fins 16 are arranged in spaced parallel relationship in substantial parallel alignment with the air flow. The density of the fins are on the order of 8–20 fins per inch. The longitudinal profile of the individual fins is generally that of a sine wave as shown, the purpose being to promote air turbulence and increased air transfer characteristics of the coil 14. However, this form is also considered to be useful in furtherance of the function of the present invention as will be described more fully below.

The fins 16 are coated with a photocatalytic semi-conductor coating on at least one side and preferably on both sides and on the entrance and exit edges thereof. The coating may be any of various types of metal oxides such as tin dioxide ($SnO_2$), titanium dioxide ($TiO_2$), zinc oxide (ZnO), tungsten trioxide ($WO_3$), lead oxide (PbO), iron titanium trioxide ($FeTiO_3$), vanadium pentoxide ($V_2O_5$), iron oxide ($Fe_2O_3$). Titanium dioxide is a preferred coating because: it has an optical absorption band close to visible light and therefore is readily activated by ultraviolet (UV) light with wave lengths less than about 400 nanometers; it is not readily poisoned by compounds in the air such as organic pollutants, it does not self-oxidize or evaporate; and it is inexpensive, stable, and environmentally sound. The coating can be applied to an otherwise finished evaporator coil but is preferably applied to the fin stock prior to its being assembled into the finished coil structure.

As will be seen, the UV lamp 21 is placed downstream of the coil 14 and is preferably aligned in parallel relationship with the tubes 14 so as to illuminate the individual fins 16 substantially equally. The lamp 21 is designed and optimized for operation within a 40–45° F., high humidity environment, and one in which there is a moving air stream. Typical output ratings at 45° F. and at a 400 FPM air flow are 120 microwatts per square centimeter at a one meter range. Although the invention is shown with a single lamp, multiple lamps may be used. In general, a single lamp is used for every 8–10 square feet of coil face area.

Because of the need for the coated fins to be irradiated by the UV light, it should be recognized that the wavy longitudinal pattern of the fins 16 lends itself to increased illumination characteristics because of the reflectivity that occurs on the variable geometry surfaces of the fins. That is, the effectiveness of the lamp 21 in its illumination of the coatings on the fins 16 is substantially enhanced over an installation wherein flat fins would be used.

The photocatalytic reaction is also enhanced by the wavy shape of the coated fins which produce turbulence in the contaminated air flowing through the coil maximizing fin contact by the airborne microbial particles.

Other features can also be used to make the light more effective in its irradiation of the coated surfaces. For example, the unit may be formed with a double wall, with sheet metal on the outside and fiberglass insulation on the inside. A second skin made of a reflective material, such as aluminum foil, can thereby be placed on the inner side of the insulation in order to reflect the light inwardly toward the fin surfaces of the coil.

Although the present invention has been shown and described with respect to a preferred embodiment, it will be understood by those skilled in the art that various changes in the form and detail thereof can be made without departing from the true spirit and scope of the invention. For example, although the invention is shown with the lamps located downstream of the coil, it should be understood that they could be placed in the upstream position as well.

What is claimed is:

1. An air conditioning system of the type having a heat exchanger coil with a plurality of fins which are in heat exchange contact with a plurality of tubes comprising:
    a fan for causing air to be passed through the heat exchange coil to be conditioned by the exchange of heat therewith;
    a coating of a photocatalytic semi-conductor material being disposed on a surface of said plurality of fins; and
    a light source disposed in optical proximity to said coated fins and having a wave length capable of activating said photocatalytic semi-conductor material.

2. An air conditioning system as set forth in claim 1 wherein said light source is disposed on a side of said coil that is downstream of said air flow through said coil.

3. An air conditioning system as set forth in claim 1 wherein said fins are in generally parallel alignment in the general direction of the air flow.

4. An air conditioning system as set forth in claim 1 wherein said light source is comprised of at least one linear lamp.

5. An air conditioning system as set forth in claim 4 wherein said linear lamp is aligned in substantial parallel relationship with the tubes.

6. An air conditioning system as set forth in claim 1 wherein said photocatalytic semi-conductor material is titanium dioxide.

7. An air conditioning system as set forth in claim 1 wherein said coating is disposed on at least one side of each of said fins.

8. An air conditioning system as set forth in claim 7 wherein said coating is disposed on both sides of each of said fins.

9. An improved heat exchanger coil of the type having a plurality of fins aligned in generally parallel relationship and spaced apart to facilitate the flow of air therethrough, and a plurality of tubes passing through openings in said fins, said tubes adapted to carry a flow of refrigerant therethrough, wherein the improvement comprises:
    a coating applied to a surface on said fins, said coating containing a photocatalytic semi-conductor material which is activatable by light so as to be capable of dissociating water molecules to form hydroxial radicals for oxidizing organic pollutants that may be on said fins or in the air passing through said fins.

10. A heat exchanger coil as set forth in claim 9 wherein said coating is titanium dioxide.

11. A heat exchanger coil as set forth in claim 9 wherein said coating is disposed on at least one side of each of said fins.

12. A heat exchanger coil as set forth in claim 11 wherein said coating is disposed on both sides of each of said fins.

13. A method of treating an air flow through a heat exchanger coil having fins and refrigerant tubes in heat exchange relationship, comprising the steps of:

coating a surface of the fins with a photocatalytic semi-conductor material;

irradiating the fin surfaces with a light source having a wave length capable of activating said photocatalytic semi-conductor material; and causing air to pass through said evaporator coil so as to be exposed to and purified by said activated photocatalytic semi-conductor material.

14. The method as set forth in claim 13 wherein said coating is titanium dioxide.

15. The method as set forth in claim 13 wherein said coating is applied to at least one side of each of the fins.

16. The method as set forth in claim 15 wherein said coating is applied to both sides of each of said fins.

17. The method as set forth in claim 13 wherein said irradiating step is accomplished with a UV ultraviolet light source.

18. The method as set forth in claim 13 wherein said irradiating step occurs on the side of said coil which is downstream from the air passing therethrough.

* * * * *